United States Patent [19]

Foss et al.

[11] 4,357,824

[45] Nov. 9, 1982

[54] METHOD FOR DETERMINING VOLATILIZATION RATES OF DISSOLVED VOLATILES FROM SOLID WASTE MATERIALS

[75] Inventors: Stephen D. Foss; Sheng H. Lin, both of Pittsfield, Mass.

[73] Assignee: General Electric Company, N.Y.

[21] Appl. No.: 187,323

[22] Filed: Sep. 15, 1980

[51] Int. Cl.³ .............................................. G01N 7/16
[52] U.S. Cl. ....................................... 73/19; 73/61.3; 374/54
[58] Field of Search ................... 73/19, 64.2, 61.3, 53, 73/17 A

[56] References Cited

U.S. PATENT DOCUMENTS

| | | | |
|---|---|---|---|
| 2,736,190 | 2/1956 | Bockelmann et al. | 73/53 X |
| 2,995,922 | 8/1961 | Firth et al. | 73/19 X |
| 3,390,568 | 7/1968 | Taylor | 73/19 |
| 3,521,478 | 7/1970 | Magorien | 73/19 |
| 3,527,085 | 9/1970 | Silas et al. | 73/64.2 |

FOREIGN PATENT DOCUMENTS 1418112  10/1965  France .................................... 73/19

Primary Examiner—Edward R. Kazenske
Assistant Examiner—Joseph W. Roskos
Attorney, Agent, or Firm—Robert A. Cahill

[57] ABSTRACT

A cylinder containing a vacuum lid opening at one end and a tee connector is used as a containment vessel to measure the rate of volatilization of dissolved volatiles from solids. One end of the tee is connected to a vacuum pump and the other end is attached to a vacuum pressure gauge. A thermal sensor is located at the bottom end of the cylinder for monitoring the temperature of the solid material. In operation, a sample of contaminated solid is placed in the cylinder, the vacuum pump is activated and the vacuum pressure and solid temperature are monitored over a period of time. The mass transport coefficient for volatilization of dissolved gases from contaminated solids can be determined from Henry's law and a mass transport equation.

2 Claims, 4 Drawing Figures

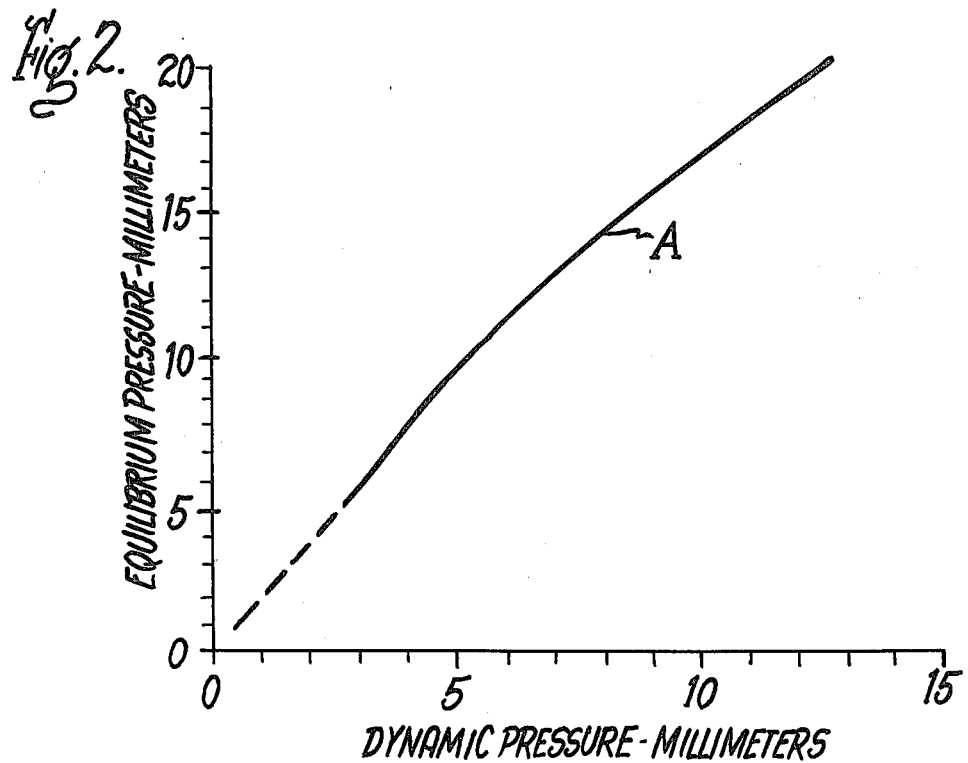
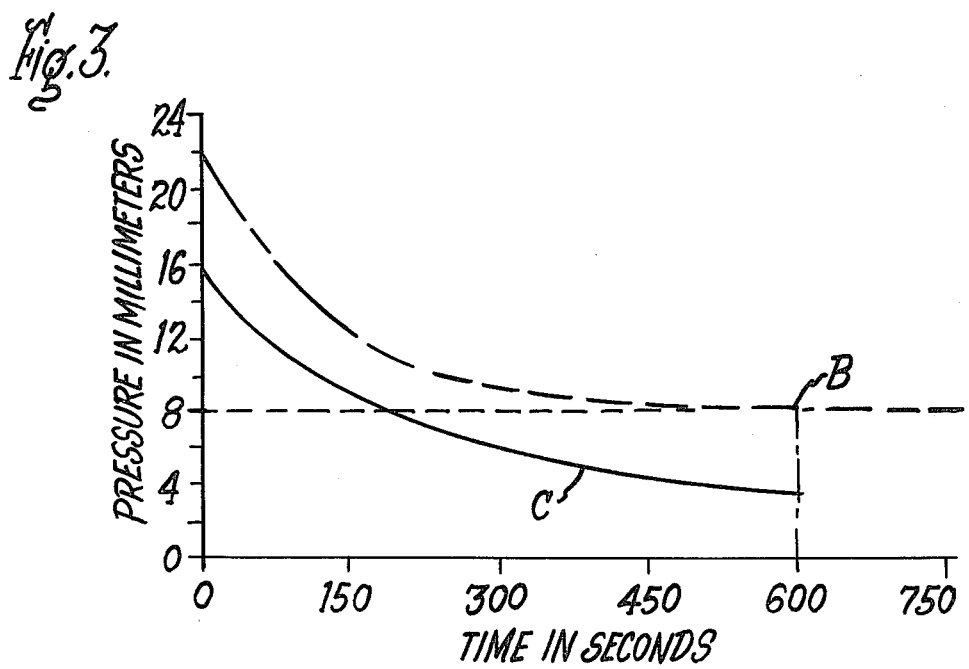

METHOD FOR DETERMINING VOLATILIZATION RATES OF DISSOLVED VOLATILES FROM SOLID WASTE MATERIALS

BACKGROUND OF THE INVENTION

The amount of contaminated volatile materials emanating from solid waste materials is a recognized concern of industry. In recent years regulations have been established by EPA and OSHA concerning the nature and concentration of toxic chemicals within the atmosphere. Since the rate of volatilization of gaseous chemicals from solid waste directly affects the concentration of contaminants in the atmosphere, primarily in the vicinity of the solid wastes, a rapid and inexpensive method for establishing the rate of volatilization of toxic species is desired. Methods currently available involve complicated gas chromatographic techniques which are difficult to use on site.

The purpose of this invention is to provide a simple method for establishing the magnitude of volatilization rates of the contaminant species in order to rapidly assess the criticality of the situation.

SUMMARY OF THE INVENTION

The invention comprises the combination of a vacuum cylinder, a vacuum calibrated pressure gauge, a vacuum pumping device and a temperature sensing element. A sample of contaminated solid is placed in the vacuum cylinder and the vacuum pump is activated. The dynamic pressure and sample temperature are then monitored as a function of vacuum treat time. Since a correlation exists between equilibrium pressure and dynamic pressure, the mass transfer coefficient can be calculated directly from the equilibrium pressure and temperature data.

BRIEF DESCRIPTION OF THE DRAWINGS

FIG. 2 is a graphic representation of the relationship between the dynamic pressure and the equilibrium pressure of volatile gaseous components using the apparatus FIG. 1;

FIG. 3 is a graphic representation of both the dynamic and equilibrium pressures as a function of time.

DESCRIPTION OF THE PREFERRED EMBODIMENT

Figure 1:
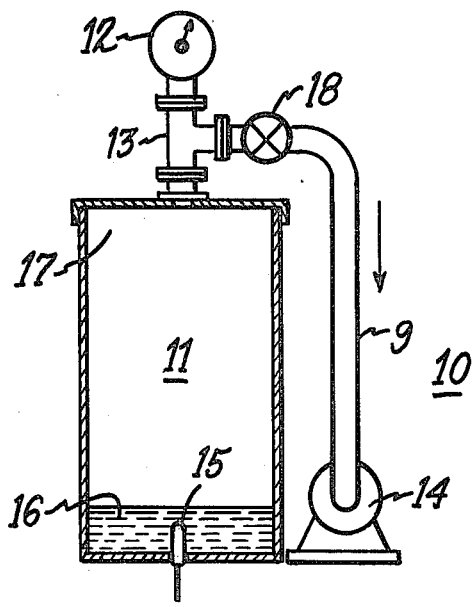
FIG. 1 is a front view in partial section of the volatilization rate measuring apparatus of the invention.

FIG. 1 shows the sampling system 10 consisting of vacuum cylinder 11, vacuum gauge 12, tee connector 13, pipe 9, vacuum pump 14, and temperature sensor 15.

Sampling cylinder 11 is partially filled with a contaminated solid sample 16 in a manner to provide a free evaporation surface essentially equivalent to that of the cross section of cylinder 11. Vacuum pump 14 is activated and vacuum pressure gauge 12 and temperature sensor 15 are monitored as a function of time.

A correlation is found to exist relating to the dynamic pressure $P_D$, which is measured while pump 14 is operating, and the equilibrium pressure $P_E$ which is determined with the pump 14 valved off from cylinder 11 by means of valve 18. Equilibrium pressure $P_E$ is defined as the sum of the partial pressures exerted by the volatile components contained within solid material 16. Henry's law which governs the relationship between the concentration of volatile contaminants within the solid material 16, and the partial pressure exerted by the contaminants which evolve in the gas phase, is given as follows:

$$X_i = H_i(T) P_i$$

where $X_i$ is the mass fraction of contaminant i in solid material 16, $H_i(T)$ is the Henry's Law partitioning coefficient relating ratio of contaminants in solid sample 16 in equilibrium with the contaminants which evolve in the vapor state. Henry constant $H_i(T)$ is temperature dependent. $P_i$ is the partial pressure exerted by contaminant i in the vapor state.

The correlation that exists between $P_D$ and $P_E$ is obtained by placing a sample of contaminated solid 16 in cylinder 11 and activating vacuum pump 14 with valve 18 in an open position. Gauge 12 is observed until no further change in pressure occurs, $P_D$ and temperature are then recorded. Valve 18 is now closed to allow equilibrium to establish. Pressure readout on gauge 12 is noted until no further change is observed, $P_E$ and temperature are then recorded. This procedure is repeated until sufficient data is established to correlate $P_D$ with $P_E$. FIG. 2 is a graphic representation of correlation A between $P_D$ and $P_E$. Once correlation A has been established the apparatus 10 of FIG. 1 can be used to directly determine $P_D$; $P_E$ can then be determined from curve A in FIG. 2 as follows. A sample of contaminated solid sample 16 is introduced within cylinder 11, vacuum lid 17 is sealed, pump 14 is activated and valve 18 is opened. As described earlier, pressure readout is monitored at gauge 12 until a dynamic equilibrium is established, that is, the pressure at gauge 18 no longer changes. Temperature and pressure readings are taken, the pressure corresponds to $P_D$. $P_E$ is read from curve A in FIG. 2. $P_E$ represents the partial pressure that coincides with the dynamic equilibrium balance between the rate of diffusion of the volatile contaminants from sample 16 and the vacuum pumping capacity of pump 14.

The fundamental mass transport relation governing the rate of volatilization of all volatile species from solid sample 16 is given by $$dP_E/dt = A_c K_v(T) [P_E - P_{EF}] \qquad (1)$$

$P_E$ therefore, represents the equilibrium pressures exerted by all volatile contaminants emanating from solid sample 16. $P_{EF}$ is the final diffusion limited equilibrium pressure of system 10, $dP_E/dt$ is the rate of change of the equilibrium pressure, $K_v(T)$ is the vacuum treat mass transfer coefficient of the volatile contaminants from solid sample 16 and $A_c$ is the ratio of the contact surface area to the gas volume. T is the measured temperature of solid sample 16.

To determine $P_{EF}$, the final equilibrium pressure, reference is made to FIG. 3 which contains the pressure readings obtained from gauge 12 as a function of time for both the equilibrium pressure data points B and the dynamic pressure date points C. $P_{EF}$ is defined as the lowest value of pressure achieved at equilibrium as shown by the slashed line in FIG. 3. The data points C for the dynamic pressure $P_D$ is obtained by observing the pressure readings on gauge 12 as described earlier.

The data points B for $P_E$ are taken from Curve A in FIG. 2.

Figure 4:
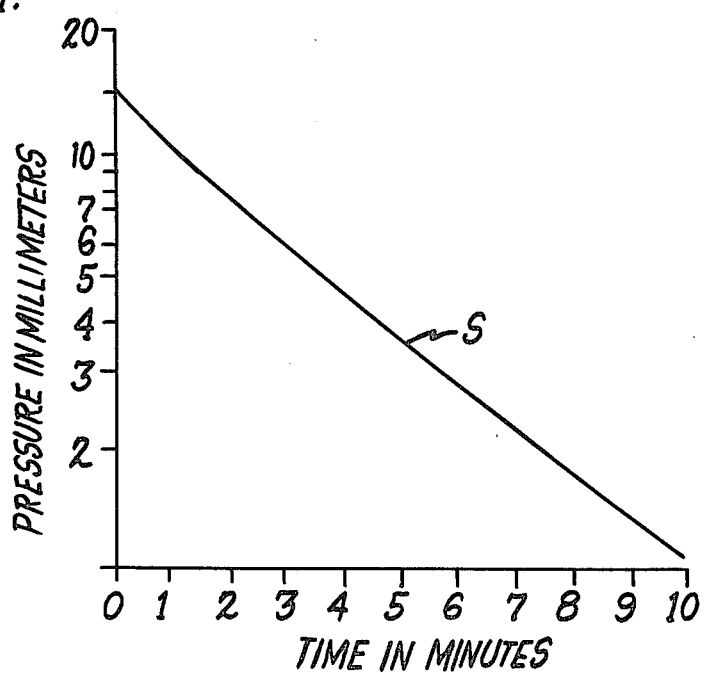
FIG. 4 is a graphic representation of the difference between the equilibrium pressure of the volatile gaseous components and the final diffusion limited equilibrium pressure as a function of vacuum treat time.

FIG. 4 is a plot of the logarithmic difference between the equilibrium pressure $P_E$ and the final diffusion limited equilibrium pressure $P_{EF}$ versus vacuum treat time. The logarithmic relationship was obtained by integrating equation (1) above, for isothermal conditions.

FIG. 4 is directly related to the mean vacuum treat mass transfer coefficient, $K_v(T)$. To estimate the mass transfer coefficient, $K(T_a)$, under atmospheric conditions, the following transformation relation is employed.

$$K(T_a) = K_v(T) \, (\pi(T_a)/\pi(T)) \, (P_{EO}/P_t) \tag{2}$$

where $K_v(T)$ is the average slope obtained from FIG. 4, $\pi(T_a)$ is the sum of the vapor pressures of the critical contaminants evaluated at ambient temperature, $\pi(T)$ is the sum of vapor pressures of the critical contaminants evaluated at the vacuum temperature condition, $P_{EO}$ is the initial equilibrium pressure at the beginning of test and $P_t$ is the atmospheric pressure.

Table I shows a comparison of measured values of the mass transfer coefficient, $K(T)$, of volatile contaminants i found in solid sample 16 of sludge material at a temperature of 20° C.

TABLE I

| Term | Value | Method |
|---|---|---|
| $K_v$ (10° C.) | 13.8 Ft./Hr. | Vacuum test data (FIG. 4) |
| $K$ (20° C.) | 0.59 Ft./Hr. | Calculated (Equation (2)) |
| $K$ (20° C.) | 0.87 ± 0.43 Ft./Hr. | Measured and Calculated (Gas Chromatography) |

Vapor pressure data on the various species of known volatile contaminants i was acquired as a function of temperature from *The Properties of Gases and Liquids*, Reid, Prausnitz and Sherwood.

An estimate of the rate of volatilization of contaminants i into the atmosphere can be calculated directly knowing the mass transfer coefficient, K.

The volatilization rate ($R_v$) is directly related to the mass transfer coefficient $K(T_a)$ at ambient temperature $T_a$, the density $d_s$ of solid sample 16, the concentration of dissolved contaminants $X_o$ and the total amount of free surface, $A_s$, available for volatilization.

$$R_v = K(T_a) \, d_s X_o A_s \tag{3}$$

The foregoing calculations show, therefore, that the system depicted in FIG. 1 can be employed to determine the rate of volatility of contaminants found at various levels beneath the earth's surface.

Once the information shown in FIGS. 2-4 is acquired, samples of solid contaminants 16 can be obtained from various positions along the surface of a test site as well as at various locations beneath the surface. System 10, shown in FIG. 1, can be employed on site to obtain rapid measurements of dynamic pressure $P_D$ emanating from the various volatile contaminants obtained at various depths L beneath the site surface.

It is within the scope of the instant invention to obtain samples of soil and sludge from a test site and transfer the samples to a main processing laboratory having a plurality of systems 10 operating simultaneously to give a complete survey of the nature of the severity of evolution contaminants into the atmosphere from any specific test site.

We claim:

1. A method for determining the volatilization rate of dissolved contaminants in a solid substance comprising the steps of:
    placing a solid substance sample in an evacuation chamber;
    evacuating said chamber by pumping;
    determining the dynamic pressure within the chamber as a function of time while pumping until said dynamic pressure reaches a substantially constant value;
    periodically halting the pumping and allowing the pressure within the chamber to come to an equilibrium pressure;
    establishing a relationship between said dynamic pressure and said equilibrium pressure; and
    monitoring the temperature of the solid substance as a function of time;
    whereby to provide data for determining the mass transfer coefficient and volatilization rate for dissolved gaseous contaminants in the solid substance.

2. The method of claim 1, which further includes the steps of:
    placing a second solid substance sample in the chamber;
    evacuating said chamber by pumping;
    determining the dynamic pressure within the chamber as a function of time;
    determining the equilibrium pressure from said established dynamic-equilibrium pressure relationship.

* * * * *